United States Patent [19]

Collins

[11] 4,250,754
[45] Feb. 17, 1981

[54] SAMPLER FOR A HOT LIQUID AND CONNECTOR THEREFOR

[76] Inventor: William J. Collins, 7005 Madison St., Merrillville, Ind. 46410

[21] Appl. No.: 37,325

[22] Filed: May 9, 1979

Related U.S. Application Data

[63] Continuation-in-part of Ser. No. 855,365, Nov. 28, 1977, abandoned.

[51] Int. Cl.³ .............................................. G01N 1/12
[52] U.S. Cl. .............................................. 73/425.4 R
[58] Field of Search ................... 73/425.4 R, DIG. 9

[56] References Cited

U.S. PATENT DOCUMENTS

| | | | |
|---|---|---|---|
| 3,415,124 | 12/1968 | Collins | 73/425.4 |
| 3,646,816 | 3/1972 | Hance | 73/DIG. 9 |
| 3,693,449 | 9/1972 | Collins | 73/DIG. 9 |
| 4,002,073 | 1/1977 | Collins | 73/DIG. 9 |
| 4,037,478 | 7/1977 | Cure | 73/DIG. 9 |
| 4,046,016 | 9/1977 | Hackett | 73/425.4 R |
| 4,069,715 | 1/1978 | Falk | 73/425.4 R |
| 4,077,264 | 3/1978 | McDevitt | 73/425.4 R |

Primary Examiner—S. Clement Swisher
Attorney, Agent, or Firm—Charles S. Penfold

[57] ABSTRACT

A molten metal sampling device is provided with a tubular connector within its rearwardly extending housing to frictionally engage a correspondingly shaped lance. Certain embodiments provide a socket for holding a sample receiver disposed for reception of a sample from the side.

42 Claims, 18 Drawing Figures

SAMPLER FOR A HOT LIQUID AND CONNECTOR THEREFOR

The subject invention embodies improved principles of design and construction and preferably comprises, among other things, an outer elongated housing having a front extremity in which is mounted a device for determining a condition of or obtaining a sample of hot liquid, such as molten material and a rear extremity which is provided with internal elongated means which has predetermined cross-sectional dimensions for slidably accommodating an end of a lance.

The device for obtaining a sample preferably comprises a pair of sections which are held in an assembled relation by a casing or sleeve to form a mold or cavity for receiving a sample of molten material, and a tube of Pyrex, or equivalent material, which has an inner extremity held between the sections and an outer extremity for initially receiving the molten material for flow into the mold. The sections are preferably provided with channel portions which provide a tubular formation which receives the inner extremity of the tube.

A particular object is to provide a setup in which the elements or formations may abut the inner end of the casing, the casing is provided with abutment means for limiting rear movement of the mold and/or, under certain conditions, limit forward movement of a lance into a formation, and either of the formations may be utilized to slidably accommodate a lance.

Also, an important object is to form the mass of refractory material about the tube and so that a frontal portion thereof is tapered and overlies front marginal edges of the housing and casing whereby to facilitate penetration of the device into the molten material and protect said edges.

A specific object is to provide an organization or structure in which the housing casing, socket and elements or formations are all of a multi-sided character whereby to promote assembly of the components and minimize the profile of the structure to facilitate safe introduction of the structure into the molten metal.

Another specific object is to provide the tube with a disintegratable cap which may be utilized in certain situations whereby to prevent entry of slag into the tube when the latter is inserted into the molten metal.

A further specific object is to provide an outer housing having forwardly extending projections which straddle the entrance portion of the tube for protecting the same, including a cap on the tube when required.

A particularly important object is to provide unique structure whereby the device for obtaining a sample of molten material can be mounted at various angles in a front extremity of an elongated support or outer housing.

Additional objects and advantages of the invention reside in providing components which can be economically manufactured and assembled on a production basis to produce a fabricated structure which has proven satisfactory and efficient in use in obtaining a sample of molten material and which allows for rapid disassembly or breakage or certain of the components to afford access to a solid sample after same has been obtained.

DESCRIPTION OF FIGS. 1–7

Figure 1:
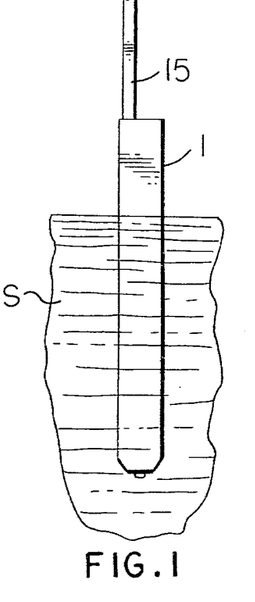
FIG. 1 is a partial view showing the structure being utilized to obtain a sample of molten material from a supply of such material in a vessel not shown.
Figures 2, 3:
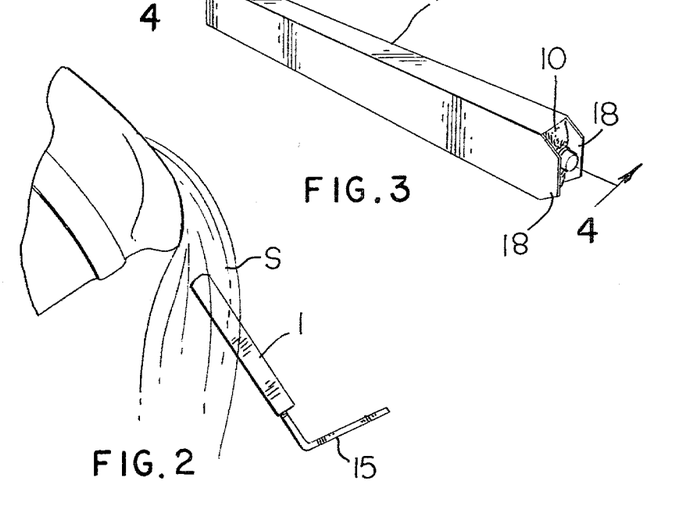
FIG. 2 is a partial view showing the structure being utilized to obtain a sample of molten material from a flowing stream thereof.
FIG. 3 is a perspective view of the structure.

Referring first to the embodiment of the invention disclosed in FIGS. 1 through 7 there is disclosed structure in FIG. 1 which is being employed to obtain a sample of molten material from a supply S thereof and FIG. 2 shows a sample being obtained from a flowing stream S of molten material. The structure comprises an elongated outer housing 1, a device generally designated 2 which includes a tubular casing 3, a mold comprising a pair of sections 4 forming a cavity or chamber 5, and integral extended channel portions 6 (one shown) which provide a tubular formation. An inner extremity of a tubular means such as a tube 7, of Pyrex or other suitable material, is secured in this formation and an outer extremity extends forwardly for initially receiving an inflow of the molten material through the tube into the chamber 5 of the mold. The sections 4 are preferably constructed of molded powdered metal but any material suitable for the purpose may be utilized.

A partition or support 8 is secured in the casing, preferably against the tubular formation, and is provided with a central aperture through which the tube 7 extends. A mass of refractory material 9 is preferably molded into the casing, about the tube and against the partition and so that its outer portion 10 is more or less flush with the marginal end edges of the housing and casing as clearly depicted in FIG. 4. This mass of refractory material serves to stabilize and protect the tube and assembled structure. It may be stated that the partition divides the casing into a front compartment which receives the mass 9 and a rear compartment which receives the mold.

Figure 4:
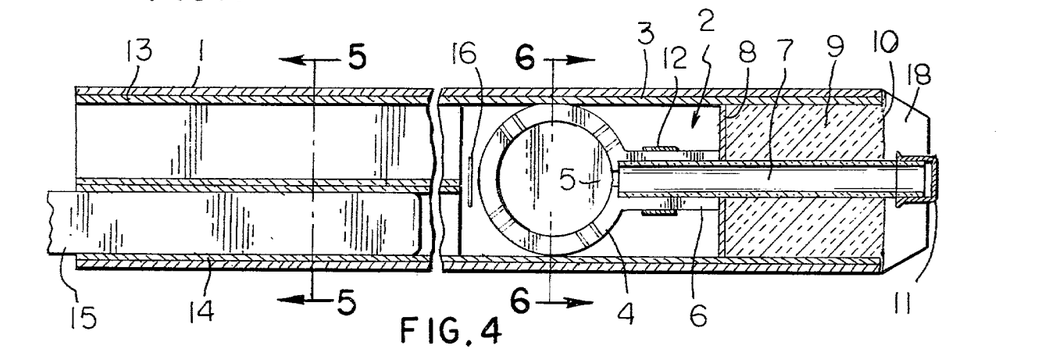
FIG. 4 is a horizontal section taken substantially on line 4—4 of FIG. 3.
Figure 5:
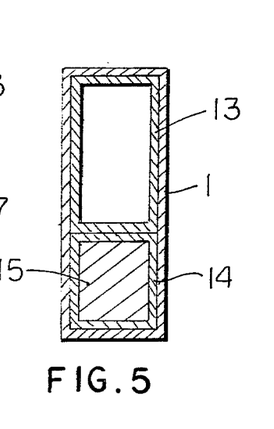
FIG. 5 is a transverse section taken substantially on line 5—5 of FIG. 4.
Figure 6:
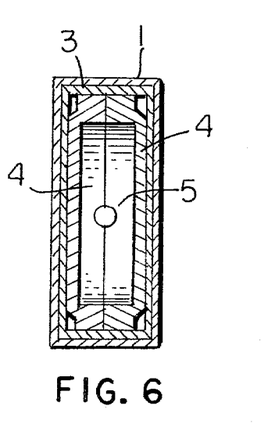
FIG. 6 is a transverse section taken substantially on line 6—6 of FIG. 4.

A disintegratable cap 11 is preferably secured over the entrance end of the tube 7 to protect and prevent entry of any foreign matter into the tube when it is initially inserted in the molten material or hot liquid.

Although the mass of material 9 is preferably molded in the casing about the tube, it can be pre-molded and press fitted into place and/or secured by a suitable cement. If pre-molded, a hole would be provided for the tube.

Attention is directed to the fact that the casing 3 may be secured in the housing in any suitable manner, such, as for example, by press-fitting and/or cementing and that the sections 4 are held in a generally assembled relation by the casing 3 and suitable tape means, such as 12, may also be utilized to obtain a more efficient assembly of these sections.

As stated above, the device for obtaining a sample is disposed in a front extremity of the housing and that means are secured in its rear extremity for slidably accommodating an end of a lance.

More particularly in this regard, a pair of means, such as tubular elements 13 and 14 as formations, are secured in the rear extremity of the outer housing and against the inner end of the casing 3. The element 13 serves as a vent or flue to facilitate release of air from the chamber 5 when it receives molten material and the element 14 serves to slidably accommodate a multisided fore end of a lance 15 for manipulating the structure for use in obtaining a sample of molten material from a supply thereof, irrespective whether the structure is utilized to obtain a sample by introduction downwardly into a mass of molten material S in a vessel, in a vertical stream S or a horizontal flowing stream thereof. Obviously, the lance may be straight as depicted in FIG. 1 or angled as shown in FIG. 2. The element 13, as shown, may have larger cross-sectional dimensions than the element 14. These elements are preferably multi-sided or quadrilateral in cross-section and constructed of a suitable non-metallic material, such as pasteboard or equivalent material, and can be press-fitted, cemented in place in a side-by-side relation and/or against the casing, or otherwise secured in the rear extremity of the housing.

Figure 8:
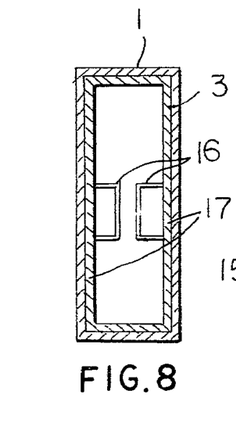
FIG. 8 is a transverse section taken through the structure to show one of the details thereof.

Attention is directed to the fact that the rear end of the casing 3 is provided with a pair of abutment means 16, preferably in the form of staples which are respectively secured to opposite side walls 17 of the casing as depicted in FIGS. 4 and 8. This abutment means affords step means limiting inward movement of the assembled mold sections 4 and the partition 8 and mass 9 of refractory material serves to limit its forward movement. More specifically, it may be stated that the partition 8 serves to divide the casing into a rear area within which the mold sections 4 are disposed and into a front area within which a portion of the tube 7 and mass 9 are disposed. The void areas about the mold sections assist in insulating these sections in addition to those portions of the housing and casing about these sections.

Attention is also directed to the fact that the casing 3, mold sections 4, tube 7, partition 8 and mass 9 constitute a subassembly or unit which is slidably inserted into the fore extremity of the outer housing 1.

As depicted in FIGS. 3 and 4, the fore ends of side walls of the housing preferably extend forwardly of the frontal surface of the mass 9 so as to provide what may be termed wings 18 which straddle that portion of the tubular means 7 which projects beyond the mass whereby to protect the entrance each of the means and the cap 11 carried thereby.

Figure 7:
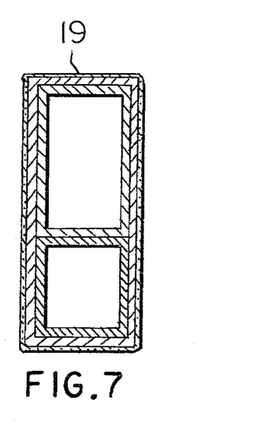
FIG. 7 is a transverse section of a modified construction, similar to FIG. 5, showing a layer of ceramic material applied thereto.

In some applications it is desirable to protect the structure by more or less encasing it in a layer or sheath of insulation, such as for example, ceramic material 19 as illustrated in FIG. 7.

Figures 9, 10:
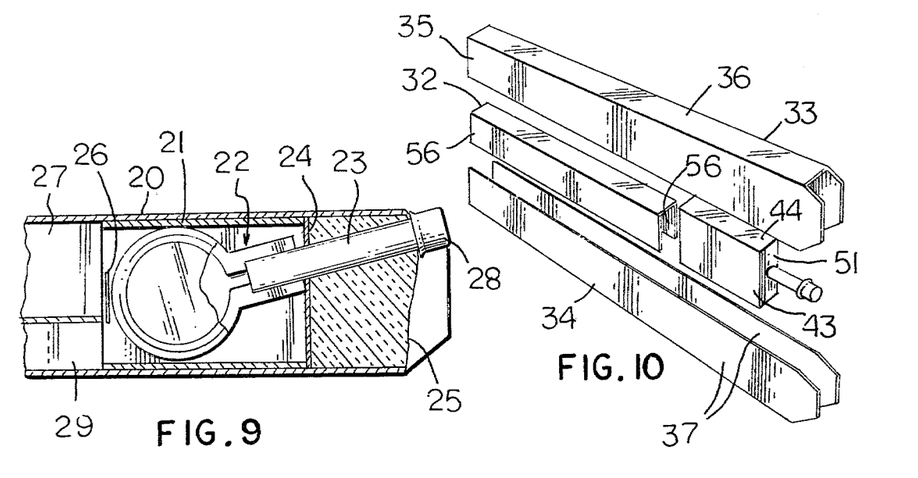
FIG. 9 is a partial horizontal section of a modified structure.
FIG. 10 is a perspective view of the disassembled components of FIG. 11.

DESCRIPTION—FIG. 9

Referring to FIG. 9 there is disclosed a modified structure comprising an outer elongated housing 20; an inner casing 21; a device generally designated 22 disposed in the casing 21 and provided with tubular means 23; a partition 24; a mass of refractory material 25; abutment means 26; a tubular element or formation 27; and a cap 28 carried by the tubular means 23. These components 20, 21, 22, 23, 24, 25, 26, 27 and 28 respectively substantially correspond to or are similar to the components 1, 3, 2, 7, 8, 9, 16, 13 and 11 described above.

Attention is directed to the fact that the structure depicted in FIG. 9 primarily differs from the structure shown in FIG. 4 by locating the device 22 at an angle or tilted position with reference to the longitudinal axis of the structure so that its entrance is located at the upper portion of the mass 25 so as to facilitate entry of molten material from a stream thereof. The device 22 is held in the angled position by the casing, partition and mass and between the partition and abutment means 26.

The structure of FIG. 9 also differs from the device 2 of FIG. 4 by utilizing a single element 27, as compared to the pair of elements 13 and 14, above referred to. Otherwise expressed, the element 27 is so disposed that a lower wall portion thereof in combination with lower portions of the outer housing provide an elongated formation 29 for slidably accommodating a lance.

Attention is also directed to the fact that the outer housing casing and element 27 are preferably multi-sided and constructed of pasteboard or any material suitable for the purpose and that the components may be secured together in any way, such as by staples or cement, to provide structure which is practical for the use intended.

DESCRIPTION FIGS. 10–13

Referring to FIGS. 10, 11, 12 and 13, there is disclosed a modified structure which shows, among other things, an outer housing generally designated 30, an inner casing generally designated 31, and an element 32 which may be fabricated.

Figure 11:
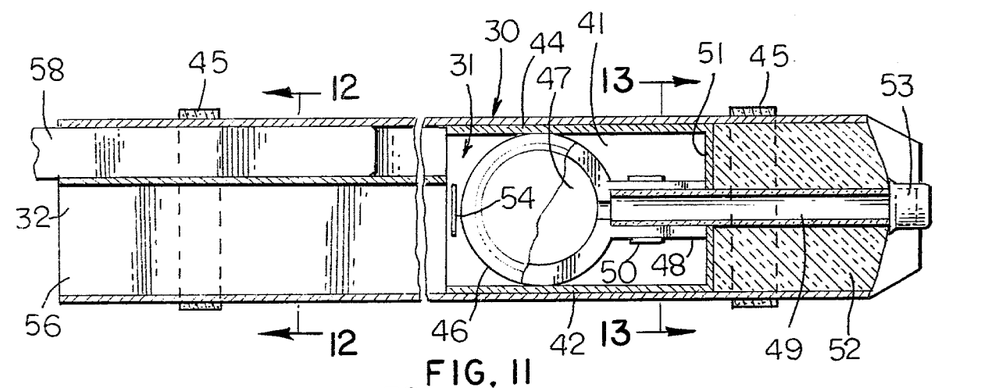
FIG. 11 is a horizontal section of the assembled structure of FIG. 10.
Figure 12:
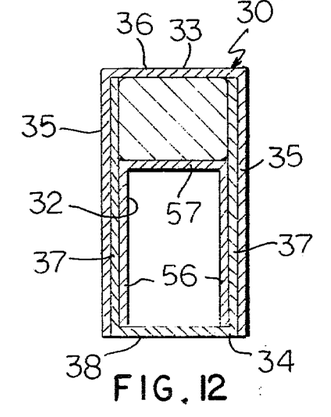
FIG. 12 is a transverse section taken substantially on line 12—12 of FIG. 11.
Figure 13:
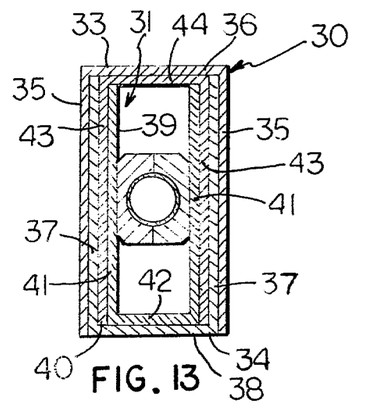
FIG. 13 is a transverse section taken substantially on line 13—13 of FIG. 11.

More particularly in this regard, the housing 30 is comprised of a pair of complementary outer and inner channel members 33 and 34 which are assembled or secured together in a nesting or cooperative relationship, with the member 34 being disposed substantially within the confines of the member 33 and bottomed therein. The outer member 33 comprises a pair of planar substantially parallel side walls 35 and a planar top wall 36 and the inner member 34 with a pair of side walls 37 and a bottom wall 38, the arrangement being such that the bottom walls are disposed in a parallel relation and the walls 37 of the inner member 34 engage the inner surfaces of the walls 35 of the outer member to provide the tubular housing having double side walls which impart strength or stability to the housing.

The casing 31 is similarly fabricated by a pair of complementary inner and outer channel members 39 and 40 which are assembled or secured in a nesting relationship. The inner member 39 comprises a pair of side walls 41 and a bottom wall 42 and the outer member 40 comprises a pair of side walls 43 and a bottom wall 44, as clearly depicted in FIG. 13.

The complementary inner and outer members of the housing may be assembled to constitute a subassembly or unit and the casing may also be assembled to constitute a subassembly or unit. The units may be respectively held assembled or in combination by any means suitable for the purpose. Staples have proven satisfactory in some applications but, if so desired, cement or tape can be utilized. As shown in FIG. 11, for example, tape 45 is banded about the housing 30.

A device 46 is disposed in the casing 31 and comprises a pair of complementary sections which form a primary chamber 47 for receiving a sample of molten material and a tubular formation 48 which receives an inner extremity of a tubular means 49 which is held in place by tape 50 surrounding the formation. A partition 51 is disposed in the housing 30 and abuts the formation 48 and a mass of refractory material 52 is placed in the housing against the partition in surrounding relation to the tubular means 49 for supporting the same. A cap 53 is carried by the means 49. It should be observed that the side walls of the inner and outer members of the housing are preferably extended beyond the mass 52 in straddling relationship to the cap and that portion of the tubular means 49 which extends forwardly of the mass for protective purposes. Forward movement of the device 46 is limited by the partition 51 and mass and rear movement of the device may be limited by abutment means 54 which is similar to the abutment means 16 above referred to.

The element 32, alluded to above, is preferably of channel shape and pressfitted into the rear extremity of the inner member 34 of the housing and against the casing and comprises a pair of side walls 56 and a top wall 57 so that this top wall and the upper portions of the side walls 37 of member 34 and top wall 36 of the outer member 33 of the housing, in combination, provide a formation for slidably accommodating a lance 58.

The cross dimensions of the pairs of channel members comprising the casing 31, and the cross dimensions of the enlarged portions of the device 46 are preferably such that these channel members when correctly assembled will substantially clamp or grip the device whereby to firmly hold it in place and its sections assembled, and that when the channel members of the housing are correctly assembled these members will substantially clamp or grip the casing whereby to firmly hold it in place in the housing. These holding factors may be sufficient without utilizing the limiting means, such as the abutment means 54 and partition 51 described above or all may be utilized if so desired to provide substantial composite structure.

All of the pairs of the channel members are preferably constructed of pasteboard or equivalent material which is of sufficient strength, thickness or durability to withstand the intense heat of molten metal for a sufficient period of time to permit penetration of the structure into the metal to obtain a sample thereof and remove it without complete destruction or disintegration of the outer housing. Otherwise expressed, the outer housing will deteriorate or become charred to some extent but not sufficiently to release the mold and sample therein. This deterioration also serves to facilitate breakage of the housing and to obtain access to the mold after a sample has been obtained.

In certain situations or uses the housing may be coated with an external layer of ceramic material as depicted in FIG. 7 for protective purposes and in other situations the channel members of the housing may be constructed from a suitable metal or metallic material. It should be understood that the shape or size of the member 32 may be modified, so that, for example, the size of the formation for accommodating the lance may be varied. Also, if desired, the position of the member 32 may be reversed to provide a lower formation, in view of the upper one shown, for receiving a lance. The formation or area which is not utilized for a lance serves as a flue or vent for the molten metal receiving the device.

It should also be understood that, if found desirable, the partitions of FIGS. 4, 9 and 11 may be eliminated, in which event, a mass of refractory or equivalent material may be worked into the casings 3, 21 and 31 about the devices 2, 22 and 46.

The description which follows is primarily directed to three modified or different structures exemplified in FIGS. 14 through 18 and these are related to the structures described in FIGS. 1 through 3 but differ therefrom to the extent that the devices or means for receiving molten material are disposed or secured to elongated outer housings at angles with reference to the longitudinal axis of the housings, as distinguished from the devices in FIGS. 1 through 13 which are secured longitudinally substantially within the confines of a front extremity of an outer elongated housing.

Figure 14:
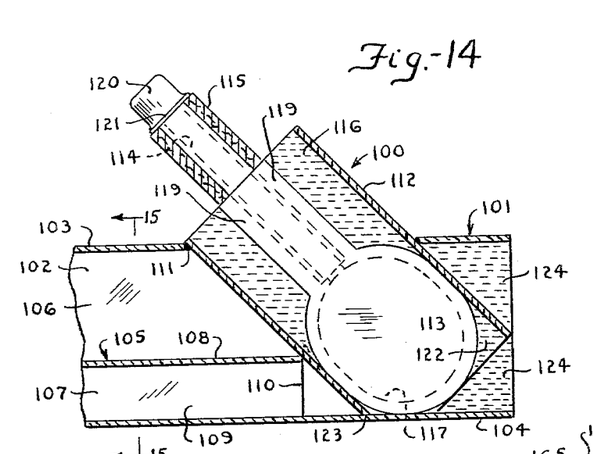
FIG. 14 is a partial vertical section taken through a modified structure.
Figure 15:
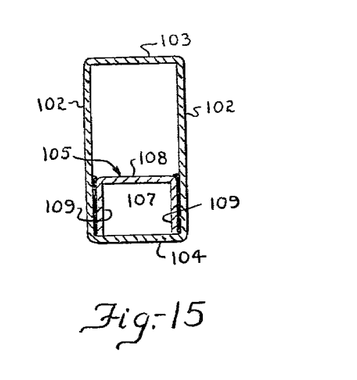
FIG. 15 is a transverse vertical section taken substantially on line 15—15 of FIG. 14.

More particularly, FIGS. 14 and 15 illustrate structure which comprises an elongated device generally designated 100 and an elongated tubular housing generally designated 101, preferably of a multi-sided character having a pair of relatively wide opposed parallel side walls 102 and a pair of narrow upper and lower walls 103 and 104 which define a housing of rectangular cross-section.

The housing 101 is preferably provided with an elongated channel member generally designated 105 which is secured lengthwise in the housing to form an opening 106 and a tubular formation 107 for slidably accommodating a lance whereby to facilitate manipulation of the housing and device 100. The channel member 105 may be secured in the housing in any mode desired, such as by a press fit, staples and/or an adhesive. This member has a top wall 108 and a pair of side walls 109 the latter of which intimately engage the side walls 102 and the marginal edges preferably by a press fit. It should be noted that this cap has a radial flange 121 which preferably engages the marginal end edge of the sleeve 115 for protecting it.

Attention is directed to the fact that the housing 101, channel member 105, tubular casing 112 and tubular sleeve 115 are all preferably constructed of a cellulosic material, such as pasteboard, but if desired these components may be made from other materials suitable for the purpose. The housing, channel member and casing are also preferably multi-sided or generally rectangular in cross-section.

It should be observed that the mold sections are preferably of a size to snugly fit in the casing 112; that an additional mass of insulating material or cement 122 is disposed in the casing to assist in holding and protecting the sections; and that a corner of the casing is preferably bevelled as indicated at 123.

The device 100 is readily assemblable with the housing by inserting it into the cutout or opening 111 so that longitudinally spaced portions of the rear inclined side of the device will respectively engage a rear marginal edge of the opening 111, the abutment means 110 of the channel 105 and the bottom wall 104 of the housing, the bevel 123 constituting one of these portions. When the device is so positioned or located, the front open extremity of the housing is then preferably filled with masses of insulating material or cement 124 whereby to assist in fixedly securing or anchoring the device so that it is substantially held at an oblique angle with reference to the longitudinal axis of the housing for use in obtaining a sample of molten material from a supply thereof.

The organization is preferably such that, if desired, the channel member can be shortened and secured so that the abutment means 110 can be moved farther to the rear; that the length of the opening 111 can be shortened; and that the angle of the bevel 123 can be modified whereby the device can be secured in any one of an infinite range of acute or oblique angular positions with respect to the longitudinal axis of the housing. Also, if desired, it may be only necessary to relocate the abutment means 110, in which event, a greater portion of the device can be extended outwardly through the opening 111 and so that additional cement can be inserted into the housing.

Furthermore, if so desired, the device can be secured to the housing by applying layers or quantities of an adhesive between the side walls of the housing and device, in which event, the need for the masses of cement 124 will not be required.

Figure 16:
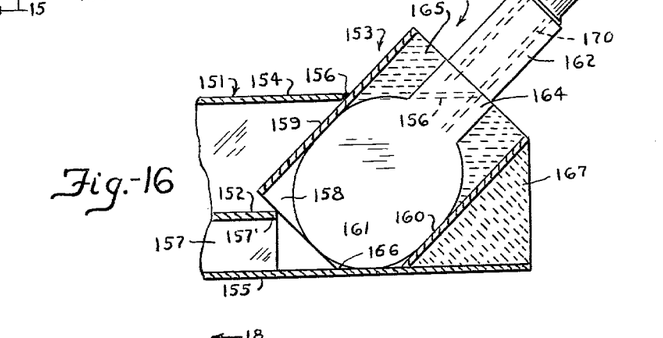
FIG. 16 is a partial vertical section of a modified structure.

The structure 150 illustrated in FIG. 16 includes an outer housing generally designated 151, a channel member 152 and a device generally designated 153 which respectively substantially correspond to the housing 101, channel member 105 and device 100 of FIGS. 14 and 15.

More specifically, the outer housing 151 comprises a pair of parallel side walls and top and bottom walls 154 and 155, the former preferably being provided with a cutout or opening 156. The channel member 152 in combination with the housing forms a tubular formation 157 like the formation 107 of FIGS. 14 and 15. The fore end of this channel provides abutment means 157'.

The device 153 comprises a casing having a pair of parallel side walls 158 (one shown) and upper and lower walls 159 and 160, a pair of mold sections 161 (one shown), an inlet tube 170, an outer sleeve 162 surrounding an outer extremity of the tube and a cap 163. The mold sections 161 have channel portions 164 which are somewhat shorter than the channels 119 of the sections of FIG. 14 and the front internal area of the casing is preferably filled with a mass of cement 165 surrounding portions of the sections. An inner corner of the casing is preferably bevelled as indicated at 166.

When the device 153 is correctedly assembled with the outer casing 151, it will be located substantially in its front extremity and extends into the cutout 156 and engages an inner marginal edge thereof, the side walls of the casing will engage the abutment means 157', the bevel 166 will engage the bottom wall 155 of the housing so that when a mass of cement 167 is placed in the housing the device will be located in a forwardly extending inclined oblique or acute angular position with reference to the longitudinal axis of the housing for use in obtaining a sample of molten material, as distinguished from the device 100 of FIG. 14 which is inclined rearwardly.

It will be observed that upper corner portions of the side walls of the housing 151 are preferably removed or cut away to generally conform to the front planar surface of the cement 165 and marginal edges of the casing. It is to be understood that the device 153 can be located in different angular portions by merely adjusting and securing the channel member 152 in different positions, and modifying the angle of the bevel 166 and adding or decreasing the size of the mass of cement 165. It is to be further understood that the device 153 can be secured to the housing 151 in different ways as described above with respect to FIG. 14.

Figure 17:
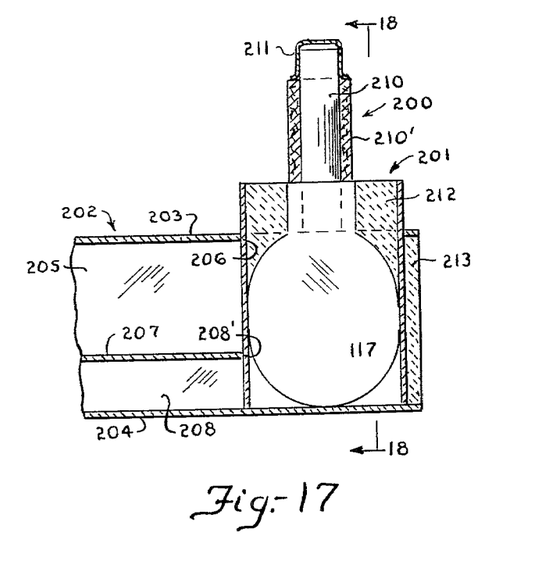
FIG. 17 is a partial vertical section of a modified structure.
Figure 18:
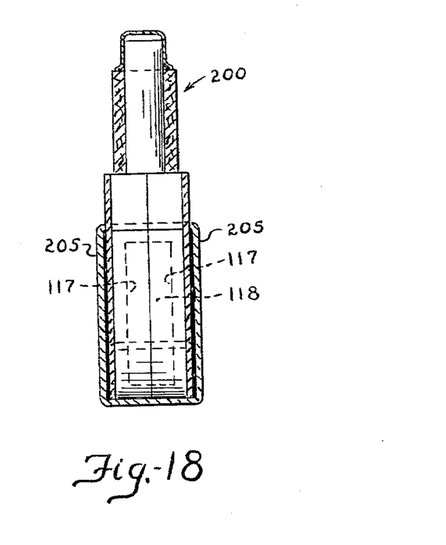
FIG. 18 is a transverse vertical section taken substantially on line 18—18 of FIG. 17.

The modified structure 200 exemplified in FIGS. 17 and 18 is similar to the structures of FIGS. 14 and 16 but is primarily different therefrom by securing a device generally designated 201 substantially at right angles or perpendicular to the longitudinal axis of an outer housing generally of the walls 109 engage the bottom wall 104 in the manner depicted in FIG. 15. The top wall 108, side walls 109 and the bottom wall 104 define the formation 107. It should be noted that the fore end of the formation 107 is preferably inset a predetermined distance from the front end of the housing 101 to provide abutment means 110.

The front extremity of the housing 101 is preferably constructed to provide structure for accommodating the device 100. More particularly, in this regard, the top wall 103 is preferably provided with a cutout or opening 111 which is inset a predetermined distance inwardly from the front marginal end edges of the housing.

The device 100 for obtaining a sample of molten material may be designed and constructed as desired but is preferably comprised of a tubular casing or member 112, a pair of mating mold sections 113 like those shown in FIG. 18, a tubular inlet or tube 114 of non-metallic material, such as Pyrex, a tubular sleeve 115, and a mass of insulating material or cement 116 disposed in the casing in sufficient quantity whereby to assist in securing the sections together and holding them in the casing.

The sections 113 are provided with recesses 117 which form a primary chamber 118 like those shown in FIG. 18 for receiving a sample of molten material and these sections also have lateral channel portions 119 (one shown) which form a tubular formation within which an inner extremity of the tubular inlet 114 is secured. The outer extremity of the inlet extends forwardly of the mass 116 and is preferably surrounded by the tubular sleeve 115 for protecting and stabilizing this extremity. The inlet 114 also extends a short distance beyond the sleeve 115 and carries a cap or closure 120 which is detachably connected to the inlet, designated 202.

More particularly, the housing 202 comprises upper and lower walls 203 and 204 and side walls 205 which substantially correspond to the walls of the housings of FIGS. 14 and 16. The upper wall 203 is preferably provided with a cutout or opening 206 for accommodating the device 201. The housing is provided with a channel member 207 forming a tubular formation 208 for a lance and an abutment means 208'. The device 201 has an outer casing 209, mold sections having recesses 117 forming a chamber 118 for receiving molten material and channels forming a tubular formation for an inner extremity of a tubular inlet 210, sleeve 210', a cap 211 on the inlet and a mass of cement 212 in the top internal area of the casing surrounding portions of the sections for holding them assembled and within the confines of the casing. The device extends through the opening 206 into the fore extremity of the housing and engages the marginal edges of the opening so that a rear wall of the casing engages the abutment means 208' and the lower marginal edges of the walls of the casing engage the bottom wall 204 of the housing. A mass of cement 213 fills a fore internal area of the housing and engages the device whereby to assist in holding the device and housing assembled for use. It is to be understood that the device can be readily located in any desired perpendicular position by merely relocating the opening 206 and the abutment means 208'.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. Means for connecting a lance and a device for obtaining a sample of liquid, said connecting means comprising wall structure forming an elongated housing having a front chamber for receiving such a device and a rear extremity, and an elongated formation mounted in said rear extremity for slidably engaging and holding a lance and extending alongside the longitudinal axis of said housing in an offset relation with respect to this axis.

2. Means for connecting a lance and a device for obtaining a sample of liquid, said connecting means comprising multi-sided wall structure forming an elongated longitudinal housing provided with an internal elongated rear offset formation for slidably engaging and holding an end of a lance and a front chamber for receiving such a device, said formation having a longitudinal axis which is offset with respect to the longitudinal axis of said housing, and said wall structure also forming an elongated tubular formation extending alongside said rear formation.

3. Means for connecting a lance and a device for determining a condition of molten material, said connecting means comprising wall structure forming an elongated straight walled housing having a front chamber for receiving such a device and a rear offset formation mounted in said housing for slidably engaging and holding a lance in said housing at one side of its longitudinal axis.

4. Means affording connection of a lance to a device for obtaining a sample of hot liquid, said connection means comprising an elongated outer housing having a fore extremity for receiving such a device and a rear extremity, said rear extremity comprising wall structure forming a pair of tubular formations arranged in a non-concentric relation whereby at least one of these formations can be utilized to slidably engage and hold an end of a lance in said housing.

5. Means for affording a connection of a lance to a device for obtaining a sample of hot liquid, said connection means comprising an elongated outer housing having a fore extremity for receiving such a device and a rear extremity, and means disposed in said rear extremity providing an elongated offset formation for a lance and a longitudinal passage extending alongside said formation providing a vent for such a device when the latter is utilized.

6. Structure of the character described comprising an elongated outer housing having a fore extremity and a rear extremity, a tubular casing disposed in said fore extremity, a partition disposed in said casing dividing it into a rear compartment and a front compartment, means disposed in said rear compartment for receiving a sample of a hot liquid, tubular means disposed in said front compartment and communicating with said receiving means through said partition for initially receiving the sample from a supply of such a liquid, means disposed in said front compartment surrounding said tubular means for stabilizing its position therein, and a pair of tubular elements disposed in said rear extremity which respectively provide a vent for said receiving means and a formation for accommodating a lance.

7. The structure defined in claim 6, in which at least one of said elements is of a multi-sided character and has a smaller cross-sectional dimension than the other element.

8. The structure defined in claim 6, in which said housing, casing and elements are all constructed of a non-metallic material.

9. The structure disposed in claim 6, including abutment means carried by said casing whereby said receiving means is held between this abutment means and said partition.

10. Structure comprising a pair of elongated complementary channel members secured together with one substantially within the confines of the other in an opposed relationship to provide an elongated tubular outer housing having a front extremity for accommodating a device for receiving a sample of hot liquid.

11. The structure defined in claim 10, in which said members are secured in a nesting relationship.

12. Structure comprising a pair of elongated complementary channel members secured together in an opposed relationship to provide an elongated tubular outer housing having a front extremity for accommodating a device for receiving a sample of hot liquid and also provide a rear extremity, and means provided in said rear extremity for slidably accommodating an end of a lance.

13. Structure comprising an outer elongated tubular housing having a front extremity for supporting means for receiving a sample of hot liquid and also having a rear extremity, and means secured in said rear extremity providing an elongated tubular formation which extends alongside the longitudinal axis of said housing in an offset relation to this axis for slidably accommodating an end of a lance.

14. A subassembly for use with a device for obtaining a sample of hot liquid, said subassembly comprising an elongated outer housing having a fore extremity for accommodating a device for obtaining a sample of a hot liquid and a rear extremity, and a pair of means disposed in said rear extremity respectively providing a vent for such a device and an offset formation for accommodating a lance.

15. The subassembly defined in claim 14, in which said housing and said pair of means are of a multi-sided character.

16. Wall structure comprising a pair of channel members of rectilinear cross sections which are assembled with one being substantially confined in the other to form an elongated casing having opposed side walls, means disposed in said casing forming a chamber for receiving a sample of hot liquid, means extending forwardly from said chamber for initially receiving such a liquid for flow into said chamber, means in said casing serving to stabilize the position of said extending means, and means secured to said side walls and extending transversely into a rear portion of said casing for limiting rear movement of said chamber means in said casing.

17. Structure for the purpose described, comprising an elongate outer housing, means disposed in an angular position in said housing for receiving a sample of molten material, a mass of refractory material secured in and engaging a fore area of said housing, a partition in said housing between said receiving means and said refractory material, and tubular means extending through said mass and having an inner extremity extending through said partition connected to said receiving means and an outer end for initially receiving a sample of a molten material for flow into said receiving means.

18. The structure defined in claim 17, including a casing disposed in said housing and about said receiving means, and offset means disposed in said housing for slidably engaging and holding a lance.

19. Wall structure for the purpose described comprising a housing having a front extremity for accommodating a device for receiving a sample of molten material from a supply thereof through forwardly extending tubular means for initially obtaining an inflow of the material, and said fore extremity being provided with substantially planar parallel means projecting in advance of and substantially straddling said tubular means for protecting the latter.

20. The wall structure defined in claim 19, in which said housing is multi-sided in cross-section and has planar side walls which constitutes said projecting means.

21. The means defined in claim 1 which is multi-sided in cross-section.

22. The means defined in claim 1, including such a device secured in said front chamber.

23. The means defined in claim 1, in which said wall structure is provided with an opening through which such a device may be extended for locating it at an oblique angle in said chamber with reference to the longitudinal axis of said housing.

24. The means defined in claim 3 which is multi-sided in cross-section.

25. The means defined in claim 4 which is multi-sided in cross-section.

26. The means defined in claim 4, including such a device secured in said fore extremity at an oblique angle with reference to the longitudinal axis of said housing.

27. The structure defined in claim 10, in which said members are substantially multi-sided in cross-section.

28. The structure defined in claim 12, in which said front extremity is shaped to provide a socket and such a device is secured therein at an angle transverse to the longitudinal axis of said housing.

29. The structure defined in claim 13, in which said front extremity is constructed to provide a socket for accommodating a device for disposition at an angle transverse to the longitudinal axis of said housing.

30. An elongated member having wall structure forming a rear extremity for facilitating attachment of a lance thereto and a tubular front extremity of uniform cross-dimensions having a single side opening forming in combination with said wall structure a socket, and an elongated device secured in said socket at an angle with reference to the longitudinal axis of said member for use in obtaining a sample of molten material.

31. A device for obtaining a sample of molten material comprising an elongated outer housing having a front extremity and a rear extremity, means extending lengthwise in said rear extremity at one side of the longitudinal axis of said housing for engaging a lance insertable into said rear extremity, and said front extremity being provided with means disposed at an angle with respect to said axis for receiving a sample of molten material.

32. In combination: an elongated housing having a rear extremity for attachment to a lance and a front tubular extremity provided with a single side opening and an elongated device for obtaining a sample of molten material comprising structure forming an enlargement disposed entirely within the confines of said front extremity and providing a chamber and tubular structure for receiving the material for flow into the chamber, said device having an upper extremity extending through said opening so that the device is disposed at an angle with reference to the longitudinal axis of said housing.

33. The combination defined in claim 32, including spaced means in said housing for holding said device thereto.

34. An elongated device for the purpose described comprising an outer elongated tubular housing, a pair of recessed sections forming a chamber and a tubular formation communicating with said chamber, a casing secured in said housing, a mass of cement disposed in said casing engaging portions of said sections for holding them substantially within the confines of said casing, a tubular member having an inner extremity secured in said tubular formation and an outer extremity for initially receiving a sample of molten material for flow through this member into said chamber, and a sleeve surrounding said outer extremity.

35. In combination: an elongated outer housing, a subassembly comprising wall structure forming an elongated casing disposed in said housing and having a fore extremity and rear structure, means for obtaining a sample of molten material secured in said fore extremity, and said rear structure having at least a longitudinal portion thereof which is spaced inwardly from said wall structure for engagement by a lance whereby to establish a detachable connection therebetween.

36. The combination defined in claim 35, in which said rear structure is multi-sided.

37. The combination defined in claim 35, in which said rear structure is constructed to provide a pair of tubular formations, of which at least one serves to accommodate a lance.

38. The combination defined in claim 35, in which said housing and casing are non-circular in cross-section.

39. In combination: an outer elongated housing, elongated structure secured within the confines of said housing, means for receiving a sample of molten material inset from a front end of said housing and having a tubular entrance extending forwardly of said housing for receiving such a material for flow into said receiving means, a mass of insulating material disposed in said housing about said tubular entrance, and said housing having a rearwardly extending wall and said elongated structure having a wall disposed in spaced relation to said extending wall to provide a formation for accommodating a lance.

40. Means for connecting a lance and a device for obtaining a sample of liquid, said connecting means comprising wall structure forming an elongated housing having a front chamber for receiving such a device, and a rear extremity and an elongated formation disposed in said extremity in spaced relation to an inner surface thereof for slidably engaging a lance whereby to assist in holding the latter thereto.

41. Means for connecting a lance and a device for obtaining a sample of liquid, said connecting means comprising wall structure forming an elongated housing having a front chamber for receiving such a device and a rear extremity, and means disposed in said rear extremity having a longitudinal wall portion arranged in spaced relation to an inner surface of said wall structure for slidably engaging a lance whereby to assist in holding the latter against said wall portion.

42. An assembly of the character described comprising multi-sided wall structure forming an elongated casing having a front extremity and a rear extremity, a device comprising a pair of mating sections disposed in said front extremity, means surrounding portions of said sections for holding them assembled to form a chamber for receiving a sample of molten material, abutment means in said casing for limiting rear movement of said device, tubular means extending forwardly from said sections and laterally outward from said casing for receiving a sample of such a material for flow into said chamber, and a mass of insulating material disposed in said casing assisting to limit forward movement of said device in said casing.

* * * * *